United States Patent
Walton

(10) Patent No.: US 10,594,091 B2
(45) Date of Patent: Mar. 17, 2020

(54) METHOD FOR DETERMINING AN OPERATIONAL STATE OF A SUBSEA CONNECTOR UNIT

(71) Applicant: Siemens Aktiengesellschaft, Munich (DE)

(72) Inventor: Daniel Walton, Morecambe (GB)

(73) Assignee: Siemens Aktiengesellschaft, Munich (DE)

( * ) Notice: Subject to any disclaimer, the term of this patent is extended or adjusted under 35 U.S.C. 154(b) by 206 days.

(21) Appl. No.: 15/558,781

(22) PCT Filed: Mar. 21, 2016

(86) PCT No.: PCT/EP2016/056154
§ 371 (c)(1),
(2) Date: Sep. 15, 2017

(87) PCT Pub. No.: WO2016/150917
PCT Pub. Date: Sep. 29, 2016

(65) Prior Publication Data
US 2018/0076573 A1 Mar. 15, 2018

(30) Foreign Application Priority Data
Mar. 26, 2015 (EP) .................... 15161136

(51) Int. Cl.
*G01R 31/3187* (2006.01)
*H01R 13/66* (2006.01)
(Continued)

(52) U.S. Cl.
CPC ..... *H01R 13/6683* (2013.01); *E21B 33/0385* (2013.01); *E21B 41/0007* (2013.01);
(Continued)

(58) Field of Classification Search
CPC ............... G01R 31/043; G01R 31/021; G01R 31/1272; G01N 27/02; E21B 33/0385;
(Continued)

(56) References Cited

U.S. PATENT DOCUMENTS 5,883,517 A * 3/1999 Broyde ................ G01R 31/083
324/522
9,631,955 B2 * 4/2017 Campbell ............ G01D 11/245
(Continued)

FOREIGN PATENT DOCUMENTS

BR    PI1000365 A2   10/2011
EP       2302479 A2    3/2011
(Continued)

OTHER PUBLICATIONS

EP Search Report dated Oct. 26, 2015, for EP patent application No. 15161136.5.
(Continued)

*Primary Examiner* — Thang X Le
(74) *Attorney, Agent, or Firm* — Beusse Wolter Sanks & Maire

(57) ABSTRACT

A method for determining an operational state of a subsea connector unit, wherein the method includes: providing at least one operational value and/or a plurality of operational values of at least one operational parameter describing a specific operational condition at at least one selected location of the subsea connector unit and comparing the at least one provided operational value and/or the plurality of provided operational values and/or at least one derivative derived from the at least one provided operational value and/or at least one derivative derived from the plurality of provided operational values with at least one predefined reference and thus determining an operational state of the subsea connector unit on the basis of the comparison. An assembly monitors an operational state of a subsea connector unit and a subsea connector unit has the assembly.

19 Claims, 4 Drawing Sheets

(51) Int. Cl.
*E21B 41/00* (2006.01)
*H01R 13/523* (2006.01)
*E21B 33/038* (2006.01)
*E21B 47/00* (2012.01)
*G01N 27/02* (2006.01)
*G01R 31/04* (2006.01)

(52) U.S. Cl.
CPC ......... *E21B 47/0001* (2013.01); *G01N 27/02* (2013.01); *G01R 31/043* (2013.01); *H01R 13/523* (2013.01)

(58) Field of Classification Search
CPC ............. E21B 33/0355; E21B 41/0007; E21B 43/013; E21B 43/017; E21B 43/0107; E21B 47/0001; E21B 47/12; E21B 47/1025; H01R 13/523
See application file for complete search history.

(56) References Cited

U.S. PATENT DOCUMENTS

| | | | | |
|---|---|---|---|---|
| 2004/0100273 | A1* | 5/2004 | Liney | F16L 53/37 324/534 |
| 2010/0051286 | A1* | 3/2010 | McStay | E21B 33/0355 166/336 |
| 2011/0071966 | A1* | 3/2011 | Holley | G05B 23/0243 706/12 |
| 2011/0298467 | A1* | 12/2011 | Douglas | E21B 41/0007 324/509 |
| 2014/0199775 | A1* | 7/2014 | Bagley | C09D 5/08 436/163 |

FOREIGN PATENT DOCUMENTS

| | | |
|---|---|---|
| EP | 2339359 A2 | 6/2011 |
| JP | 2001006822 A | 1/2001 |
| WO | 2012041528 A1 | 4/2012 |
| WO | 2013175155 A1 | 11/2013 |

OTHER PUBLICATIONS

IPRP (PCT/416 and 409) dated May 26, 2017, for PCT/EP2016/056154.
International Search Report dated Jul. 7, 2016, for PCT/EP2016/056154.
Jon Thore Myklatun, NTNU-Trondheim, Norwegian University Science and Technology, "Condition Monitoring of Subsea Connectors", pp. 1-151, XP055221154.

* cited by examiner

METHOD FOR DETERMINING AN OPERATIONAL STATE OF A SUBSEA CONNECTOR UNIT

CROSS REFERENCE TO RELATED APPLICATIONS

This application is the US National Stage of International Application No. PCT/EP2016/056154 filed Mar. 21, 2016, and claims the benefit thereof. The International Application claims the benefit of European Application No. EP15161136 filed Mar. 26, 2015. All of the applications are incorporated by reference herein in their entirety.

FIELD OF INVENTION

The present invention relates to a method for determining an operational state of a subsea connector unit. Further, the present invention relates to an assembly for monitoring an operational state of a subsea connector unit and further to a subsea connector unit comprising such an assembly.

ART BACKGROUND

In the near future an increasing demand for communication over wide distances, especially for example between continents or with subsea oil and gas processing equipment/consumers will be needed. Hence, infrastructures, like sea cables and connectors linking subsea cables and modules, e.g. subsea modules, like transformers, pumps etc., that are located and operated error proof subsea will be essential.

Electrical connectors, interconnects and feed-throughs or penetrators, respectively, are consider to be some of the most critical components in any electrical communication and/or power distribution system. They provide a rugged and reliable method for connecting and disconnecting electrical conductors and a means for penetrating barriers and bulkheads with said conductors. Often these connectors and penetrators are employed in remote and harsh environments, with one such remote, harsh environment being subsea.

Typically, such connectors may be used for interfacing electrical distribution equipment such as transformers, switchgear and variable speed drives with rotating equipment including pumps and compressors that are routinely used in the extraction of oil and gas resources. In addition, connectors may also be used for interfacing communication systems (including analogue, Ethernet and fibre optic systems) with sensors, actuators and the like, used in the control and monitoring of oil and gas production equipment.

Although generally very robust, any connection within a system where additional leak paths and complicated mechanical assemblies are introduced will inevitably be considered a 'weak link.' The integrity of a connector is further questioned where it is mateable (or dis-connectable) whilst subsea (i.e. fully submerged in sea water).

Moreover, these devices are often complex mechanical assemblies that are subject to pressure and temperature fluctuations as well as variable electrical stresses. Modes that could lead to the failure of a connector include, but are not limited to, ingress of water into the connector, contamination of the compensating media, incorrect mating (resulting in poor electrical contact/continuity), sudden temperature increases, de-mating whilst energized, significant pressure differentials from inside to outside the connector etc. The likelihood for many of these failure modes occurring increases over time as materials are aged, thermally and/or mechanically fatigued, electrically stressed or subject to other degradation mechanisms.

The remote location and relative inaccessibility of many of the world's oil and gas producing locations precludes visual inspection and on site monitoring, and for the same reasons, any sudden failures can cause expensive and time consuming interventions.

It is currently the practice to construct the devices so that they outlast a predefined time span and after this span is reached to replace the devices. Thus, the connector is replaced after a defined period, during a routine maintenance period or after failure. However, this often results in the replacement of totally functional and still reliable devices and thus increasing costs and service efforts. Furthermore, a sudden failure can occur any time during the predicted lifetime of the device what may result in catastrophic situations.

SUMMARY OF INVENTION

It is a first objective of the present invention to provide a method that allows a reliable monitoring of the subsea connector unit and thus to provide a subsea connector unit that can be operated safely and reliably and has an extended lifespan in comparison to state of the art systems.

It is a further objective of the present invention to provide an assembly that can evaluate an operational state of the subsea connector unit dependable and repeatable.

It is still a further objective of the present invention to provide a subsea connector unit that has a long term reliability and a reduced risk for failure to occur compared with state of the art systems.

These objectives may be solved by a method, an assembly and a connector unit according to the subject-matter of the independent claims.

According to a first aspect of the present invention, a method for determining an operational state of a subsea connector unit is provided.

It is proposed, that the method comprises at least the steps of: Providing at least one operational value and/or a plurality of operational values of at least one operational parameter describing a specific operational condition at at least one selected location of the subsea connector unit and comparing the at least one provided operational value and/or the plurality of provided operational values and/or at least one derivative derived from the at least one provided operational value and/or at least one derivative derived from the plurality of provided operational values with at least one predefined reference and thus determining an operational state of the subsea connector unit on the basis of the comparison.

Due to the inventive matter, a safe, reliable and failure proof operation of the connector unit can be provided. The monitoring of the operational integrity of a connector unit, in real time, such that deterioration/degradation can be monitored and assessed with trends and comparisons being made, allows for targeted preventative maintenance to be conducted before failure occurs. Moreover, un-expected failures can be mitigate, allow for the planning of preventative maintenance and aid in the diagnostic of faults in electrical power and communication systems employed in the subsea oil and gas industry. However, should sudden failures occur, the data obtained from the condition monitoring system should also allow for the efficient location of faults in order that remedial actions can be targeted, again saving time and resource.

Even if the terms "operational value, operational parameter, location, derivative, part, compensating action, control unit, detection unit, measuring device, sensor and fibre" (see also below) are used in the singular or in a specific numeral form in the claims and the specification the scope of the patent (application) should not be restricted to the singular or the specific numeral form. It should also lie in the scope of the invention to have more than one or a plurality of the above mentioned structure(s).

A subsea connector unit is intended to mean a unit that is located subsea during operation and which physically connects at least two parts, like two subsea cables, or a subsea cable with a subsea module (e.g. a transformer, a pump etc.) or a busbar inside of the module or two modules, respectively. The subsea connector unit may be used in any harsh environment and may be embodied as an electrical connector and/or penetrator or advantageously as a wet mateable connector/penetrator, or as a connector part, e.g. as a male connector part or a female connector part. Moreover, it is advantageously employed in a high voltage application, but may also be employed in a medium voltage or low voltage application.

Such a connector unit comprises at least a conductor part that helps to establish an electrical connection in a mated position of two connected parts, like two cables or a cable with a module. This conductor part may be a conductor pin, receptacle pin or male part of a connector or of a penetrator or a socket contact of a female part, plug or socket or connector body of a connector for contacting a conductor pin of a male part. Further, the connector unit comprises connector parts that are adapted to mate physically with each other and are for example embodied as the male part and as the female part.

In this context an operational state of the connector unit is intended to mean an overall performance or state of the connector unit. The performance can vary over time or due to different conditions of the connector unit or its environment. For example, the performance can be a good performance where a good overall integrity of the connector unit is provided or an undisturbed operation could be ensured. That would be advantageous. Further, the performance might be acceptable but may have critical issues or minor discrepancies that need a closer surveillance. Moreover, the performance might be lacking so that a secure operation of the connector unit might be impossible and a de-energising or a maintenance would be needed.

Moreover, an operational condition is intended to mean an operation of the subsea connector unit under specific conditions in terms of pressure, temperature, current, voltage etc. It reflects the current properties of the operation of the subsea connector unit.

Furthermore, an operational parameter is intended to mean a physical parameter, like a pressure, temperature, current, voltage etc. or a parameter derived from at least one physical parameter, like the quality of a used fluid due to the measuring of a tan delta ($\delta$), relative humidity, a viscosity, particulate contamination etc. This fluid may be any fluid useable in a subsea connector unit and may be, for example, an insulating and/or compensating medium. An insulation medium is intended to mean any substance feasible for a person skilled in the art, like a silicone gel, grease, oil, gas. The insulation medium is used to protect and isolate internals and electrical contacts of e.g. the female part for example from salt water and debris as well as to support the mating of the female part with the male part of the connector unit. Thus, it has also lubricating properties. Moreover, the insulation medium may be also a compensation medium due to its ability to react to pressure or thermal expansion and contraction. In the case of the medium embodied as a compensation medium the medium would be combined with a metal bellows/elastomeric diaphragm compensating system.

An operational value is intended to mean an absolute or differential measurement or number obtained for one parameter. The plurality of operational values would refer all to the same parameter but differ in e.g. the time point when provided or measured. Moreover, a selected location should be understood as a location where a condition monitoring is especially of interest or relevant, for example due to changes in a contour that may cause electrical issues, poor electrical contact between pieces or high friction between pieces causing elevated temperatures or excessive pressure differentials which may cause seal failure and water ingress into the connector or abrasion that, in turn, may cause impurities in a fluid.

The term "providing" should be understood as "obtaining, measuring, reading or receiving". Hence, the at least one operational value and/or the plurality of operational values may be a measured value or a feed value or a value provided from an external source.

Furthermore, a derivative is intended to mean a result of an operation performed on the operational value or the plurality of operational values. The operation may be any operation feasible for a person skilled in the art, like a mathematical operation. The derivative may be, for example, a specific difference between at least two values or a special gradient of several values or a selected pattern of several values.

In embodiments, the term "predefined" should be understood as "selected beforehand" and/or as "being saved in a control unit to be recalled for the comparison". The reference may be any reference feasible for a person skilled in the art. The reference may be a single value or a plurality of values or a specific correlation of several values. Advantageously, the reference defines a normal behaviour of the subsea connector unit and/or a part thereof. Hence, a secure mode of the subsea connector unit is ensured. A normal behaviour is intended to mean an uncritical and secure operation of the subsea connector unit.

According to an alternative embodiment the reference defines an abnormal behaviour of the subsea connector unit and/or a part thereof. As a result, unstable and critical conditions of the subsea connector unit can be identified and suitable measures can be initiated to stop or undo the problem(s). An abnormal behaviour is intended to mean a condition where an action should be initiated to act on the subsea connector unit or its current operational state and/or when the operation of the subsea connector unit deviates from an acceptable, secure or ideal operation.

In an embodiment, the method comprises the further step of: Using the at least one provided operational value and/or the plurality of operational values as a marker for localising critical regions and/or pieces of the subsea connector unit.

In a further embodiment, the method comprises the step of: Activating at least one compensating action in case of a detection of an abnormal behaviour of the subsea connector unit and/or a part thereof. Hence, a suitable measure can be taken to prevent an unadvantageous and/or a detrimental operation and thus possible damage of the subsea connector unit or parts thereof. In this context a "compensating action" is intended to mean an action that prevents or stops certain conditions, which are critical for the integrity of the subsea connector unit or the system that the connector is part of. The compensating action may be any action feasible for a person skilled in the art, like a de-energising of the subsea connector unit, a de-mating of the subsea connector unit, an initiation of a tighter maintenance regime, an activation of a maintenance action, especially a preventative maintenance action, a reduction of a used current for the subsea connector unit. The compensating action can be actuated or triggered by any mechanism or actor suitable for a person skilled in the art, like from a control system and/or a person monitoring a control system.

The operational parameter may be any parameter feasible for a person skilled in the art. Advantageously, the operational parameter is a parameter selected out of the group consisting of: a temperature, a pressure, a humidity, a position, an electrical value (like current, voltage or resistance), a quality of a fluid, like the compensating medium or oil. Thus, a wide variety of different situations and operational scenarios can be monitored.

The temperature may be sensed using a thermistor, a thermocouple, a Pt 100/1000 or another commercially available temperature measuring device. The pressure may be sensed using a potentiometric, an inductive, a capacitive, a piezoelectric, a strain gauge based or another commercially available pressure measuring device. The condition or quality of the fluid can be, for example, determined by measuring a relative humidity, a tan δ (loss tangent), temperature, pressure, viscosity, a dielectric strength, by counting the number of particles per volume or by using another commercially available fluid condition measuring means. The measurement may for example be achieved by measuring one or more electrical properties (such as conductance, capacitance, inductance etc.) of the medium/oil via a probe across which a high frequency signal is applied. The measured value, which could be permittivity, is compared with a database value and a relative measurement obtained.

Increases in temperature may lead to aging and degradation of insulating and sealing components, particularly polymers, resulting in reduced performance and potential premature failure. Severe pressure differentials may lead to rupture of compensating diaphragms or failure of sealing elements resulting in water ingress. Contamination of a fluid, like the compensating medium, particularly when employed in an electrically stressed region of an assembly, be it particulate or moisture based, can significantly reduce the electrical properties of the fluid, leading to reduced performance or failure.

In an embodiment, the method comprises the step of: Performing the step of providing and the step of comparing of the at least one operational value and/or the plurality of operational values for several selected locations of the subsea connector unit. In other words, the same parameter is monitored at different locations of the subsea connector unit. Due to this, the overall integrity of the subsea connector unit can be monitored more precisely. In this context several locations is intended to mean more than one location. Thus the subsea connector unit comprises at least two measuring devices to detect the at least one operational value and/or the plurality of operational values at different locations/positions.

Advantageously, the method comprises the step of: Performing the step of providing and the step of comparing of the at least one operational value and/or the plurality of operational values for several different operational parameters. In other words, different parameters may be monitored especially at the same time and/or the same location. Hence, a more accurate current state of the subsea connector unit can be pictured. In this context several parameters is intended to mean more than one parameter. In this embodiment, the subsea connector unit comprises at least one measuring device that can detect at least two parameters simultaneously or in series. Alternatively, it may comprise at least two measuring devices for monitoring at least two different parameters.

In an embodiment, the method comprises the step of: Performing the step of providing and the step of comparing of the at least one operational value and/or the plurality of operational values for a first operational parameter at a first location of the subsea connector unit and performing the step of providing and the step of comparing of the at least one operational value and/or the plurality of operational values for at least a second operational parameter at at least a second location of the subsea connector unit. Consequently, a refined monitoring of the subsea connector unit can be advantageously provided.

In an embodiment, the method comprises the step of: Obtaining the at least one derivative by a statistic operation. In other words the at least one operational value and/or the plurality of operational values are trending statistically. Thus, the method can be employed on values that can be subjected to various different analyses broadening the field of application. The statistic operation may be any operation suitable for a person skilled in the art, like averaging, applying a filter operation e.g. a Gaussian filter, performing a smoothing operation e.g. building a moving average, performing a Fourier transformation.

In an embodiment the reference is a static reference, providing a defined limit that ensures a reliable operation. In this context a static reference is intended to mean a set reference that is unchangeable during the operation of the system. The static reference is derived from experienced data.

Additionally or alternatively, the reference is a dynamic reference allowing the system to react to changes of the system or its environment and thus to work in an optimised way under new conditions. In a further realisation the method comprises the step of: Adjusting the reference in dependency of the operational condition of the subsea connector unit and/or a part thereof. Hence, the operational state can be adjusted to the actual condition of the subsea connector unit.

When a first providing and comparing step results in an agreement of the provided operational value and/or the plurality of provided operational values and/or at least one derivative derived from the at least one provided operational value and/or at least one derivative derived from the plurality of provided operational values with the predefined reference defining the normal behaviour of the subsea connector unit, it may be possible to use the at least one provided operational value and/or the plurality of provided operational values obtained in the first providing and comparing step as a predefined reference in a subsequent comparing step. Moreover, it may be possible to adjust the reference in dependency of an operational history of the subsea connector unit and/or a part thereof, documented, for example, over a specific time, like three month. Hence, an aging of the subsea connector unit or parts thereof can be considered in the monitoring system.

In an embodiment, the method comprises the step of: Performing the determining of the operational state of the subsea connector unit with the help of a statistical method. Thus, the comparison can be performed with a learning system. Moreover, the comparison is easy and diffuse allowing more flexibility. The statistical method may be any method suitable for a person skilled in the art, like the use of a statistic estimator, a neural network, a fuzzy logic, a Kalman filter, a regression analysis etc. It would be also possible to determine the operational state of a part of several parts of the subsea connector with the help of a statistical method especially to determining of the operational state of the subsea connector unit.

According to a further aspect of the present invention, an assembly for monitoring an operational state of a subsea connector unit is provided.

It is proposed, that the assembly comprises at least one control unit that is embodied in such a way so that at least one provided operational value and/or a plurality of provided operational values and/or at least one derivative derived from the at least one provided operational value and/or at least one derivative derived from the plurality of provided operational values is compared with at least one predefined reference, so that a operational state of the subsea connector unit is determined.

Due to the inventive matter, a safe, reliable and failure proof operation of the connector unit can be provided. The monitoring of the operational integrity of a connector unit, in real time, such that deterioration/degradation can be monitored and assessed with trends and comparisons being made, allows for targeted preventative maintenance to be conducted before failure occurs. Moreover, un-expected failures can be mitigate, allow for the planning of preventative maintenance and aiding in the diagnostic of faults in electrical power and communication systems employed in the subsea oil and gas industry. However, should sudden failures occur, the data obtained from the condition monitoring system should also allow for the efficient location of faults in order that remedial actions can be targeted, again saving time and resource.

According to a realisation of the invention the assembly comprises at least one detection unit that is embodied in such a way to detect at least one operational parameter at at least one selected location of the subsea connector unit, resulting in the providing of an operational value and/or a plurality of operational values related to a specific operational condition. Thus, the monitoring can be easily performed.

According to a still further aspect of the present invention, a subsea connector unit is provided. The subsea connector unit may comprise at least a part of a subsea connector, for example a male part or a female part, or a penetrator. The subsea connector unit comprises at least one detection unit that comprises at least one detection device adapted to measure and to provide at least one operational value of at least one operational parameter describing a specific operational condition at at least one selected location of the subsea connector unit.

In an embodiment, the at least one detection device is arranged inside a housing of the subsea connector unit. In particular, the at least one detection device may be arranged in proximity to the respective selected location of the subsea connector unit.

In an embodiment, the subsea connector unit comprises at least one assembly in any of the above-described configurations.

In an embodiment, the assembly comprises at least one detection unit that comprises at least one detection device. Hence, the parameter can be detected constructively easy. The detection device may be embodied as any device feasible for a person skilled in the art.

In an embodiment, the at least one detection device is a sensor selected out of the group consisting of: a temperature sensor, a pressure sensor, a humidity sensor, a position sensor, a sensor for monitoring an electrical value, a sensor for monitoring a quality of a fluid. Due to this, a wide variety of parameters can be detected with well-known principles allowing a reliable measurement. For examples of possible employed sensors see listing above.

In an embodiment, the at least one senor is a fibre optic sensor. Hence, a sensor can be employed that is small in size and can be integrated easily into the subsea connector unit.

Advantageously, the fibre optic sensor is configured for electrical, thermal or mechanical measurements or in other words, the fibre optic sensor is embodied in such a way so that electrical, thermal or mechanical influences on/in the subsea connector unit can be detected. One example would be a fibre Bragg Grating sensor which can be configured to measure changes in strain, temperature etc.

In a further embodiment of the invention the subsea connector unit comprises at least one optical fibre and at least two or a plurality of fibre optic sensors, wherein the at least two or the plurality of fibre optic sensors are arranged in series within the at least one optical fibre. In other words, the at least two or the plurality of fibre optic sensors can be engineered in series within a single fibre or the at least two or the plurality of sensors can be multiplexed into a single fibre using a form of light wavelength shift or time delay sensing for each sensor. Due to this, several sensors can be arranged in a tight space providing a space saving arrangement.

The above-described characteristics, features and advantages of this invention and the manner in which they are achieved are clear and clearly understood in connection with the following description of exemplary embodiments which are explained in connection with the drawings.

BRIEF DESCRIPTION OF THE DRAWINGS

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
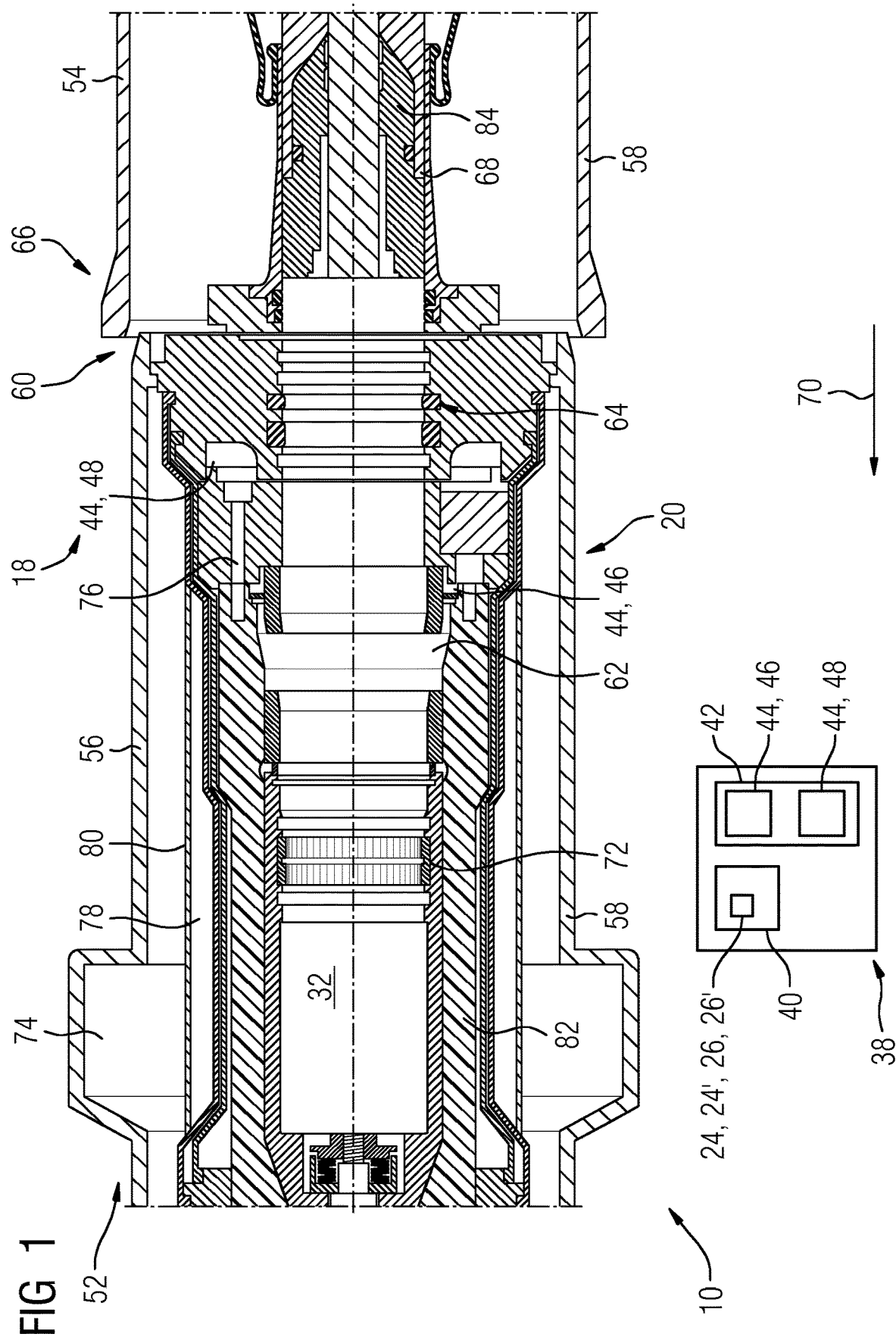
FIG. 1: shows schematically in a cross sectional view a subsea connector unit beforehand of mating with an assembly comprising a control unit and a detection unit.

The illustrations in the drawings are schematically. It is noted that in different figures, similar or identical elements are provided with the same reference signs.

FIG. 1 shows a high voltage subsea connector unit 10 for connecting two connected parts, like two subsea cables (not shown), wherein the connector unit 10 comprises a connector 52 with a male part 54 or a conductor pin 54 and a female part 56 or female socket 56. While the description below is given for a connector unit comprising a male part and a female part, it should be clear that the teachings of the present application are equally applicable to only one connector part, or to a penetrator or the like. Both the conductor pin 54 and the female socket 56 are each encased in a housing 58, which will be axially aligned during a mating or de-mating process of the male pin 54 and the female socket 56. The female socket 56 is located at a plug front end 60 of one subsea cable and comprises an axially receiving cavity 62 with seals 64 for preventing entering of water and dirt into internals of the female part 56. The male pin 54 is located at a receptacle front end 66 of the other subsea cable and comprises a receptacle pin assembly 68.

For a mating of the male pin 54 and the female socket 56 the receiving cavity 62 and the receptacle pin assembly 68 will be arranged axially aligned towards each other, so that by moving the receptacle pin assembly 68 in direction of the female socket 56 or a moving direction 70, the receptacle pin assembly 68 can partially enter the receiving cavity 62 of the female socket 56. Due to a proper positioning of the receptacle pin assembly 68 in the receiving cavity 62 of the female socket 56 an electrical connection is established between the male pin 54 and a socket contact 72 of the female socket 56.

To isolate the internals from the surrounding sea water, which can enter a section 74 of the female part 56, and to prevent seawater and debris from entering the receiving cavity 62, the receiving cavity 62 is filled with a fluid 32 or an insulation medium 32, like isolating insulation medium. The receiving cavity 62 is sealed off in the unmated condition by a shuttle pin that is pushed backwards into the female part 56 during the mating by the receptacle pin assembly 68. Due to a pushing/mating force of the male pin 54 during the mate the insulation medium 32 is displaced from the receiving cavity 62 along a distribution path 76 into a compensation volume 78 of the female part 56 (only schematically shown, see also FIG. 3).

During the operation of the subsea connector unit 10 conditions may change and may influence, especially negatively, the integrity of the subsea connector unit 10. This, in turn, could lead to the failure of the subsea connector unit 10. The conditions or modes may be an ingress of water into the connector 52, contamination of the compensating media 32, incorrect mating of the male pin 54 and the female socket 56 (resulting in poor electrical contact/continuity), sudden temperature increases, de-mating whilst energized, significant pressure differentials from inside to outside the connector 52 etc. Increases in temperature may lead to aging and degradation of insulating and sealing components 32, 64, particularly polymers, resulting in reduced performance and potential premature failure. Severe pressure differentials may lead to rupture of compensating diaphragms 80, bellows or seals of the compensation volume 78 or failure of sealing elements 64 resulting in water ingress. Contamination of compensating fluid or medium 32, often oil, particularly when employed in an electrically stressed region of the unit 10, be it particulate or moisture based, can significantly reduce the electrical properties of the oil, leading to reduced performance or failure.

Thus, the subsea connector unit 10 comprises an assembly 38 for monitoring an operational state of the subsea connector unit 10 (shown schematically in FIG. 1 outside of the connector 52 for better presentability). The assembly 38 comprises a control unit 40 and a detection unit 42 with in this exemplary embodiment two detection devices 44. This detection device 44 is a sensor 46, 48 selected out of the group consisting of: a temperature sensor for a temperature T, a pressure sensor for a pressure p, a humidity sensor for a humidity h, a position sensor for a selected position, a sensor for monitoring an electrical value (like a current A or a voltage V) or a sensor for monitoring a quality of a fluid 32, like a viscosity, a tan δ, an dielectric strength, a flow rate, a density or a Reynolds number. Thus, at least two operational parameters 14, 16 can be monitored.

The sensors 46, 48 are arranged to detect the respective parameter 14, 16 at selected locations/positions 18, 20. These positions 18, 20 are advantageously chosen to monitor critical regions, pieces or parts 28 of the connector 52 that are subjected to detrimental influences. The part 28 may be the fluid 32, the male pin 54, the diaphragm 80, the insulation 82, the seals 64 etc. For example, at position 18 the fluid 32 as a part 28 of the connector 52 passes the sensor 46 along its distribution path 76 from the cavity 62 to the compensation volume 78. The sensor 46 can detect parameters 14 of the fluid 32 during its displacement. Thus, a temperature T, a pressure p, a humidity, a viscosity, the tan δ or contaminations may be detected that may cause electrical issues e.g. during a subsequent mate-de-mate cycle of the male pin 54 and the female socket 56.

In the mated position of the male pin 54 and the female socket 56 (not shown) diameters of an insulation 84 of the female socket 56 and of a conductor 84 of the male pin 54 change at position 20. That can cause electrical issues and an elevated risk of electrical discharge. Thus, the sensor 48 monitors or measures a temperature rise which would be indicative of a high contact resistance or too high a current A at position 20 as parameter 16. Hence, the operational parameters 14, 16 describe a specific operational condition at the selected locations 18, 20 of the subsea connector unit 10.

Figure 2:
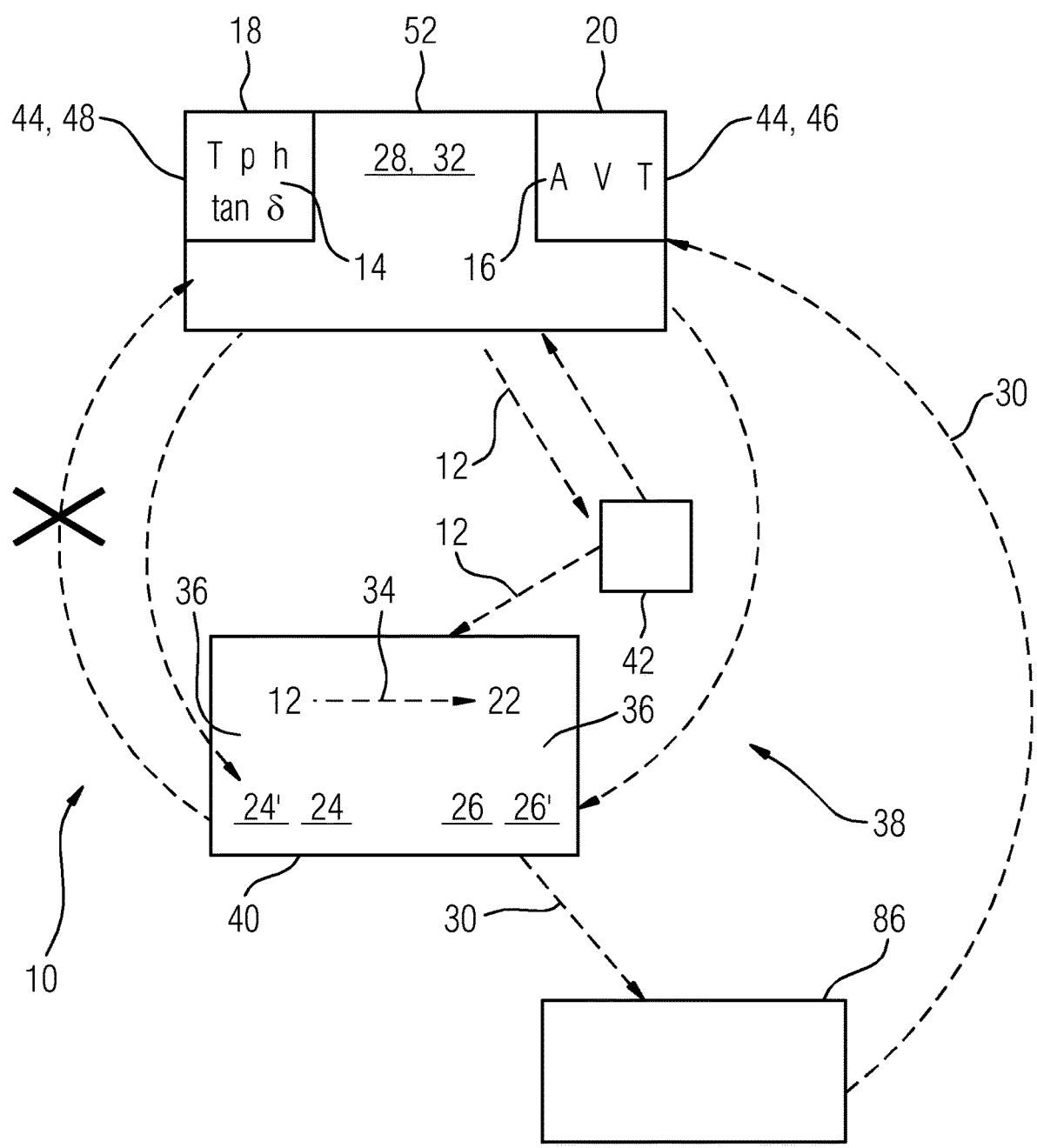
FIG. 2: shows schematically the operation principal of the method for determining an operational state of the subsea connector unit from FIG. 1, FIG. 3: shows an alternative subsea connector unit with a tan δ/temperature sensor

In the following passages, the method for determining the operational state of a subsea connector unit 10 will be described on basis of FIG. 2 that shows schematically the functional principal of the method.

The detection unit 42 monitors with its sensors 46, 48 the parameters 14, 16, like the temperature T, the pressure p, the humidity h, the tan δ of the fluid 32 or electrical parameters A, V of the connector 52 at positions 18, 20. As a result the detection unit 42 provides obtained or measured operational values 12 or a plurality of these operational values 12 of the operational parameters 14, 16 to the control unit 40. The sensor 46, 48 may work with any principle feasible for a person skilled in the art. The temperature may be sensed using a thermistor, thermocouple, Pt 100/1000 or other commercially available temperature measuring device. The pressure may be sensed using a potentiometric, inductive, capacitive, piezoelectric, strain gauge based or other commercially available pressure measuring device. The fluid 32 or oil condition may be sensed by measuring the relative humidity, tan δ (loss tangent), temperature, pressure, viscosity, direct measurement (counting) of particles per unit volume or by other commercially available oil condition measuring means.

Depending on the data input, the control unit 40 uses the operational value 12 or the plurality of operational values 12 or at least one derivative 22 derived from the provided operational value 12 and/or at least one derivative 22 derived from the plurality of provided operational values 12 for further analysis. The at least one derivative 22 may be obtained by a statistic operation 34, like an averaging, an applying of a filter operation e.g. a Gaussian filter, a performing of a smoothing operation e.g. building a moving average or a performing of a Fourier transformation. The used operation depends on the provided data and the type of parameter analysed as well as one the wanted outcome and will be chosen by a person skilled in the art according to his knowledge independently.

Further, the control unit 40 compares the provided operational value 12 or the plurality of provided operational values 12 or the at least one derivative 22 derived from the provided operational value 12 or from the plurality of provided operational values 12 with at least one predefined reference 24, 24', 26, 26'. On the basis of this comparison the operational state of the subsea connector unit 10 is determined.

Hence, the step of providing and the step of comparing of the at least one operational value 12 and/or the plurality of operational values 12 are performed for several and in this exemplarily embodiment for two selected locations 18, 20 of the subsea connector unit 10. Moreover, these steps are provided for several different operational parameters 14, 16.

The kind of used reference 24, 24', 26, 26' depends on the evaluated parameter 14, 16 and the classification of the parameter 14, 16 in respect of the risk for the subsea connector unit 10. Thus, the reference 24, 24' may define a normal behaviour of the subsea connector unit 10 and/or a part 28 thereof or the reference 26, 26' may define an abnormal behaviour of the subsea connector unit 10 and/or a part 28 thereof.

In case a normal behaviour is monitored no changes of the operational mode of the subsea connector unit 10 are needed. Hence, no further actions are initiated (shown by the crossed arrow on the left hand side of FIG. 2).

In case of a detection of an abnormal behaviour of the subsea connector unit 10 and/or of a part 28 thereof a compensating action 30 is activated and performed by an actor 86 on the subsea connector unit 10. This compensating action 30 is dependent on the detected state of the subsea connector unit 10 or the severity of the detected abnormal behaviour. For example, in case of the risk of a severe failure the compensating action can be a reduction in current A or a de-energising of the subsea connector unit 10. Minor discrepancies between the reference 24, 24', 26, 26' may be tolerated and provoke only a regime of tighter monitoring intervals. Moreover, the compensating action 30 may be the initiation of a preventive maintenance procedure.

The reference 24, 26 may be a static reference 24, 26 or in other words a reference 24, 26 that is unchanged during the operation of the subsea connector unit 10. To provide a more flexible but however still reliable operation of the subsea connector unit 10 the reference 24', 26' may be a dynamic reference 24', 26'. Such a dynamic reference 24', 26' is adjusted in dependency of the operational condition of the subsea connector unit 10 or the part 28 as shown in FIG. 2 by the two arrows pointing from the connector 52 to the control unit 40 or references 24', 26', respectively.

For example, in case a first providing and comparing step results in an agreement of the provided operational value 12 and/or the plurality of provided operational values 12 and/or the at least one derivative 22 derived from the at least one provided operational value 12 and/or at least one derivative 22 derived from the plurality of provided operational values 12 with the predefined reference 24, 24' defining the normal behaviour of the subsea connector unit 10, it may be possible to use the at least one provided operational value 12 and/or the plurality of provided operational values 12 obtained in the first providing and comparing step as a predefined reference 24' in a subsequent comparing step.

An even more flexible operation can be provided when the determining of the operational state of the subsea connector unit 10 is performed with the help of a statistical method 36. The statistical method may be any method suitable for a person skilled in the art, like the use of a statistic estimator, a neural network, a fuzzy logic, a Kalman filter, a regression analysis etc. This system allows a certain fuzziness of the monitored parameters 14, 16. For example, by evaluating five parameters 14, 16 separately they all have a certain reference 24, 24', 26, 26' used for the comparison and defining the subsequent action. In case of an evaluation of these five parameters 14, 16 together they can influence the evaluation of each separate parameter 14, 16 reciprocally. Thus, two "good" parameters 14, 16 may balance the negative influence of a "bad" parameter 16.

Consequently, the inventive method describes condition monitoring system that can be employed within a connector unit 10 or a penetrator assembly. This system would report the status/value of a measurable quantity that can be assessed against a known/idealised value. Providing or measuring the values or the plurality of values 12 in real time and trending them over time will give a quantitative indication to the integrity of the connector unit 10.

Figure 3:
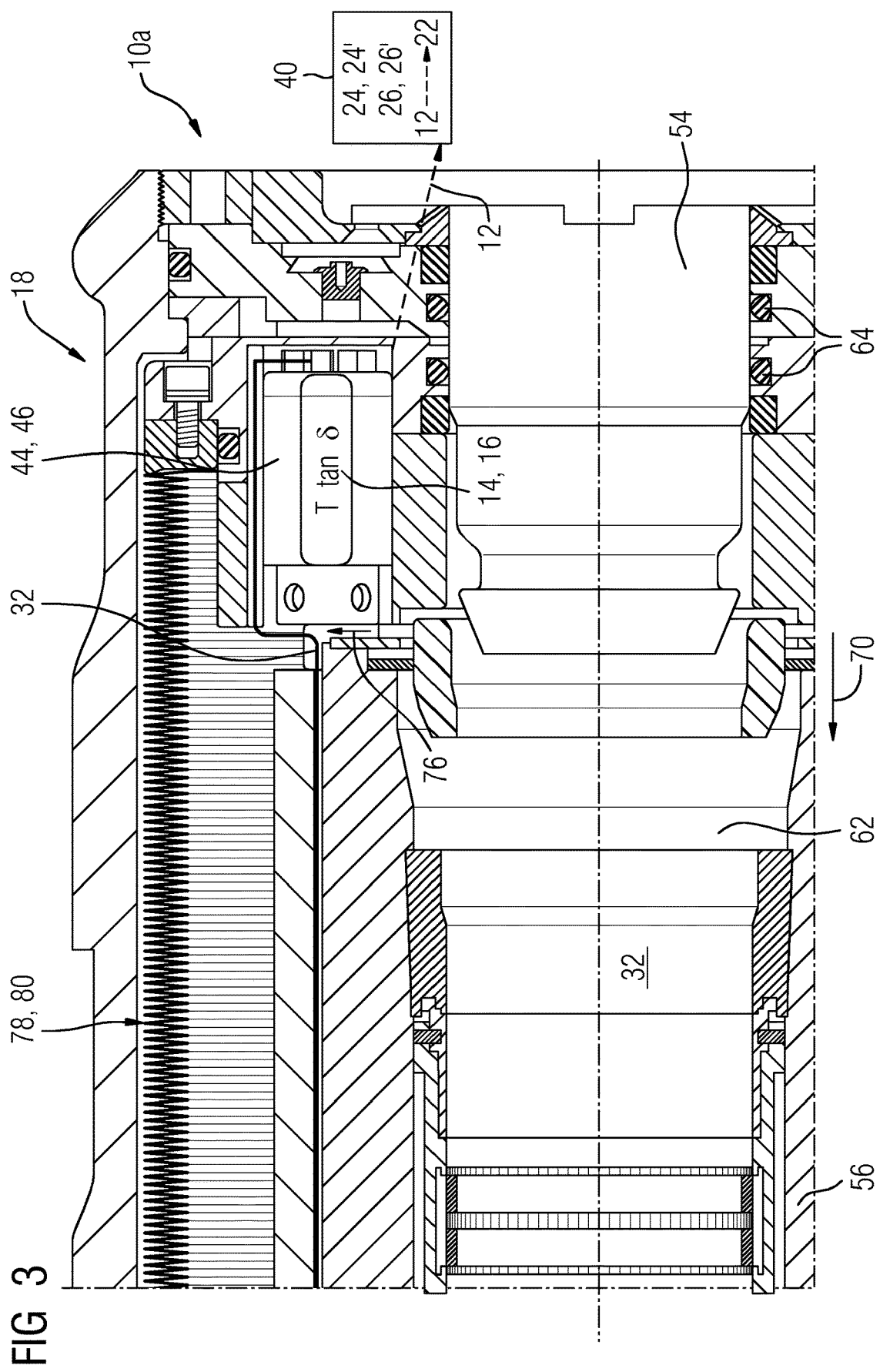
Figure 4:
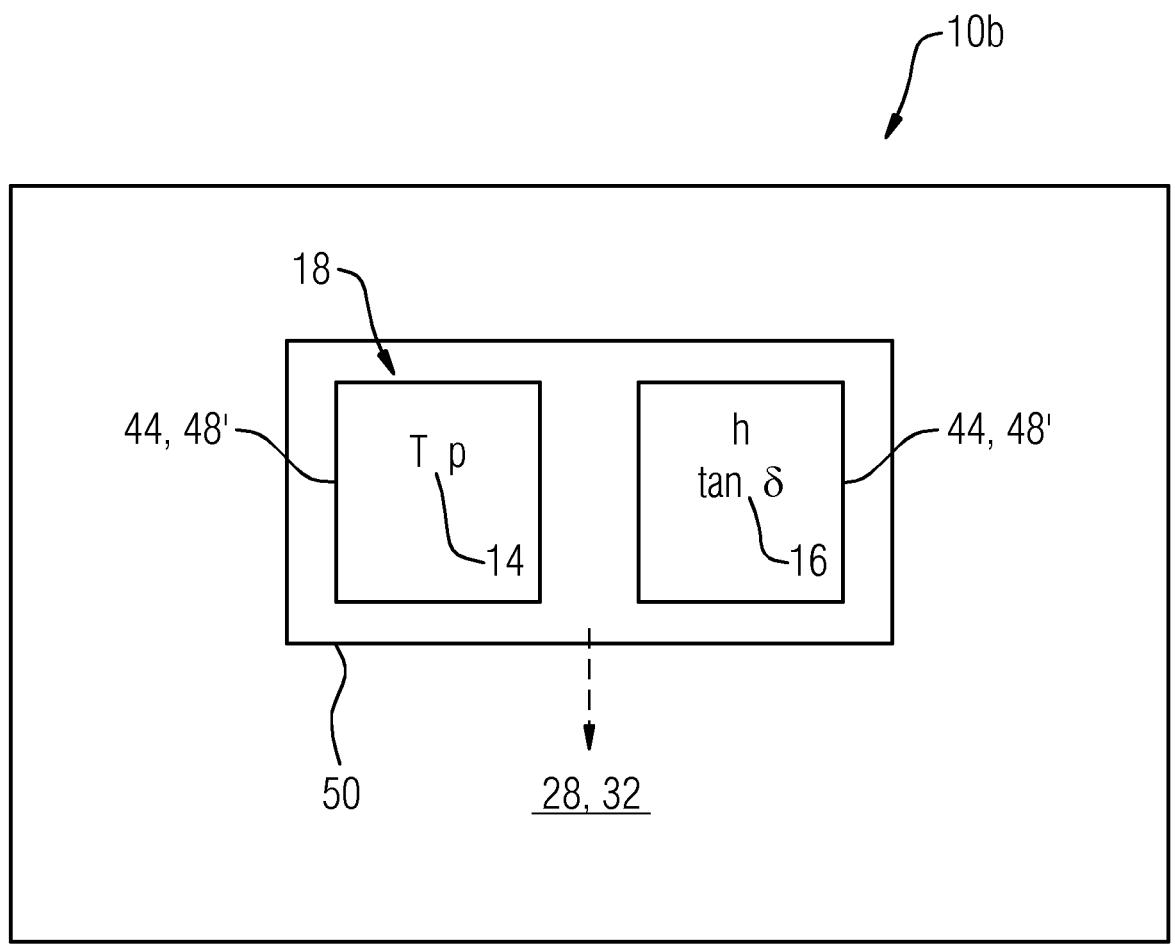
FIG. 4: shows schematically a further alternative subsea connector unit with a fibre optical sensor.

FIGS. 3 and 4 show two alternative exemplary embodiments of the subsea connector unit 10. Identical components, features and functions are denoted by the same reference numerals. However, to distinguish the exemplary embodiment of FIGS. 3 and 4 over that of FIGS. 1 and 2 the letters 'a' and 'b' have been added to the reference numerals of the components that are designed differently in the exemplary embodiment of FIGS. 3 and 4. The description below is substantially limited to these differences compared to the exemplary embodiment of FIGS. 1 and 2, wherein reference is made to the description of the exemplary embodiment in FIGS. 1 and 2 with respect to identical components, features, and functions.

FIG. 3 shows a first alternative embodiment of the subsea connector unit 10. The subsea connector unit 10a of FIG. 3 differs from the subsea connector unit 10 of FIGS. 1 and 2 in that the senor 46 is embodied as a combined tan δ and temperature T sensor 46 at position 18. Moreover, a compensation volume 78 of the subsea connector unit 10a comprises a diaphragm 80 with an accordion-like folding.

The value(s) 12 or the derivate(s) 22 relate to several parameters 14, 16 that describe a specific operational condition at a selected location 18 of the subsea connector unit 10a. The parameter 14, 16 may relate to a quality of a fluid 32, like the insulating medium 32, and the parameter 14, 16 is a temperature T and a tan δ of the fluid 32.

A cavity 62 of a female part 56 of the subsea connector unit 10a is filled with fluid 32 that is displaced by a male pin 54 during a mate of the male pin 54 and the female socket 56. The fluid 32 travels a distribution path 76 from the cavity 62 of the female part 56 to the compensation volume 78 with the diaphragm 80. Along this distribution path 76 the fluid 32 passes the sensor 46 to be analysed.

The system is monitored by a control unit 40 comprising at least one predefined reference 24, 24', 26, 26' for a comparison of the value(s) 12 or derivative(s) 22 with the reference 24, 24', 26, 26' to determine an operational state of the subsea connector unit 10a.

FIG. 4 shows in a schematical depiction a second alternative embodiment of the subsea connector unit 10. The subsea connector unit 10b of FIG. 4 differs from the subsea connector unit 10 of FIGS. 1 and 2 in that a detection device 44 or a senor 48' is embodied as a fibre optic sensor 48'. The subsea connector unit 10b comprises an optical fibre 50. In this optical fibre 50 two or a plurality of fibre optic sensors 48' can be realised, wherein the fibre optic sensors 48' are arranged in series within the optical fibre 50. Thus, with one optical fibre 50 at least one operational value 12 and/or a plurality of operational values 12 and/or derivatives 22 derived therefrom can be provided or measured.

It should be noted that the term "comprising" does not exclude other elements or steps and "a" or "an" does not

The invention claimed is:

1. A method for monitoring operational integrity of a subsea connector unit, wherein the method comprises:
   providing one or more operational values of at least one operational parameter describing a specific operational condition of a fluid used to protect electrical contacts of the subsea connector unit at one or more selected locations of the subsea connector unit;
   wherein the at least one operational parameter of the fluid comprises one of temperature, pressure, humidity, position, an electrical value, and quality; and
   comparing the one or more operational values and/or at least one derivative derived from the one or more operational values with at least one predefined reference and thus determining an operational state of the subsea connector unit on a basis of the comparison;
   wherein the one or more operational values are provided or monitored in real time.

2. The method according to claim 1,
   wherein the quality of the fluid comprises one of viscosity, loss tangent tan δ, dielectric strength, flow rate, density and Reynolds number.

3. The method according to claim 1,
   wherein the fluid comprises a compensating medium, a silicone gel, grease, oil, or gas.

4. The method according to claim 1,
   wherein the at least one predefined reference defines a normal behaviour of the subsea connector unit and/or a part thereof or the at least one predefined reference defines an abnormal behaviour of the subsea connector unit and/or the part thereof.

5. The method according to claim 4, further comprising:
   activating at least one compensating action in case of a detection of the abnormal behaviour of the subsea connector unit and/or the part thereof.

6. The method according to claim 1, further comprising:
   performing the step of providing and the step of comparing of the one or more operational values for several selected locations of the subsea connector unit.

7. The method according to claim 1, further comprising:
   performing the step of providing and the step of comparing of the one or more operational values for several different operational parameters.

8. The method according claim 1, further comprising:
   obtaining the at least one derivative by a statistic operation.

9. The method according to claim 1,
   wherein the at least one predefined reference is a static reference or the at least one predefined reference is a dynamic reference.

10. The method according to claim 9, further comprising:
    adjusting the at least one predefined reference over time in dependency of the specific operational condition of the subsea connector unit and/or a part thereof.

11. The method according to claim 1, further comprising:
    performing the determining of the operational state of the subsea connector unit with the help of a statistical method.

12. The method according to claim 1, further comprising providing a trend of the one or more operational values over time to determine a quantitative indication of the operational integrity of the subsea connector unit.

13. The method according to claim 1, further comprising:
    moving the fluid along a distribution path when mating or de-mating the electrical contacts, and
    providing the one or more operational values when mating or de-mating the electrical contacts.

14. An assembly for monitoring of the operational integrity of a subsea connector unit, comprising:
    at least one control unit that is embodied such that one or more operational values of at least one operational parameter describing a specific operational condition of a fluid used to protect electrical contacts of the subsea connector unit at one or more selected locations of the subsea connector unit and/or at least one derivative derived from the one or more operational values is compared with at least one predefined reference, so that an operational state of the subsea connector unit is determined;
    wherein the at least one operational parameter of the fluid comprises at least one of temperature, pressure, humidity, position, an electrical value, and quality; and
    wherein the one or more operational values are provided or monitored in real time, and
    wherein a trend over time is provided to give a quantitative indication of the operational integrity of the subsea connector unit.

15. The assembly according to claim 14, further comprising:
    at least one detection unit that is embodied to detect the at least one operational parameter at the one or more selected locations of the subsea connector unit, resulting in the providing of the one or more operational values related to the specific operational condition.

16. A subsea connector unit, comprising:
    an electrical connector comprising an electrical contact;
    at least one detection unit that comprises at least one detection device adapted to measure and to provide at least one operational value of at least one operational parameter describing a specific operational condition of a fluid used to protect the electrical contact at one or more selected locations of the subsea connector unit;
    wherein the at least one detection device comprises a sensor selected out of the group consisting of: a temperature sensor, a pressure sensor, a humidity sensor, a position sensor, a sensor for monitoring an electrical value, and a sensor for monitoring a quality of the fluid; and
    wherein the at least one operational value is provided or monitored in real time, and
    wherein a trend over time is provided to give a quantitative indication of an operational integrity of the subsea connector unit.

17. The subsea connector unit according to claim 16,
    wherein the at least one detection device is arranged inside a housing of the subsea connector unit.

18. The subsea connector unit according to claim 16, comprising
    an assembly for monitoring of the operational integrity of the subsea connector unit, in real time, for determining an operational state of the subsea connector unit,
    wherein the assembly comprises at least one control unit that is embodied such that the at least one operational value of the at least one operational parameter describing the specific operational condition at the one or more selected locations of the subsea connector unit and/or at least one derivative derived from the at least one operational value is compared with at least one predefined reference, so that the operational state of the subsea connector unit is determined; wherein the at least one operational parameter comprises one of temperature, pressure, humidity, position, and the quality of the fluid; and wherein the at least one operational value are provided or monitored in real time, and wherein the trend over time is provided to give the quantitative indication of the operational integrity of the subsea connector unit, and wherein the assembly further comprises the at least one detection unit.

19. The subsea connector unit according to claim 16, wherein the at least one detection device comprises a sensor comprising at least one optical fibre and at least two fibre optic sensors, wherein the at least two fibre optic sensors are arranged in series within the at least one optical fibre.

* * * * *